United States Patent [19]
Magerlein

[11] 3,969,376
[45] July 13, 1976

[54] 13,14-DIHYDRO-16-FLUORO PROSTAGLANDIN E₁ ANALOGS

[75] Inventor: Barney J. Magerlein, Portage, Mich.

[73] Assignee: The Upjohn Company, Kalamazoo, Mich.

[22] Filed: Feb. 21, 1975

[21] Appl. No.: 551,692

Related U.S. Application Data

[60] Division of Ser. No. 381,155, July 20, 1973, which is a continuation-in-part of Ser. No. 248,013, April 27, 1972, abandoned.

[52] U.S. Cl.............................. 260/408; 260/211 R; 260/247.2 R; 260/268 R; 260/293.65; 260/326.2; 260/429.9; 260/439 R; 260/448 R; 260/468 D; 260/488 R; 260/501.1; 260/501.15; 260/501.17; 260/501.2; 260/514 D

[51] Int. Cl.².................. C07C 61/38; C07C 69/74

[58] Field of Search............ 260/468 D, 514 D, 408

[56] References Cited

OTHER PUBLICATIONS

Nakanishi, et al., JACS 81 5259, (1959).

*Primary Examiner*—Robert Gerstl
*Attorney, Agent, or Firm*—Morris L. Nielsen; Robert A. Armitage

[57] ABSTRACT

Prostaglandin-type compounds with one or two fluoro substituents at the C-16 position are disclosed, with processes for making them. These compounds are useful for a variety of pharmacological purposes, including anti-ulcer, inhibition of platelet aggregation, increase of nasal patency, labor inducement at term, and wound healing.

17 Claims, No Drawings

13,14-DIHYDRO-16-FLUORO PROSTAGLANDIN E₁ ANALOGS

CROSS REFERENCE TO RELATED APPLICATIONS

This is a division of application Ser. No. 381,155, filed July 20, 1973 which is a continuation-in-part of my copending application Ser. No. 248,013 filed Apr. 27, 1972, now abandoned.

The present invention relates to prostaglandin analogs, for which the essential material constituting a disclosure thereof is incorporated by reference here from S.N. 551,694, filed February 21, 1975, now pending issuance as a U.S. Patent.

I claim:

1. An optically active compound of the formula

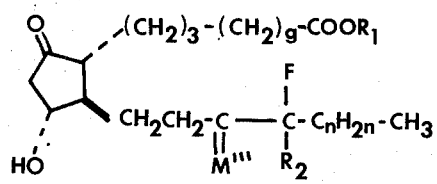

or a racemic compound of that formula and the mirror image thereof, wherein $g$ is an integer from 2 to 5, inclusive; wherein $C_nH_{2n}$ is alkylene of one to 9 carbon atoms, inclusive, with one to 6 carbon atoms, inclusive, in the chain between $-CFR_2-$ and terminal methyl; wherein $M^{III}$ is

or

wherein $R_7$ and $R_8$ are hydrogen or alkyl of one to 4 carbon atoms, inclusive, being the same or different; wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of 1 to 4 carbon atoms, inclusive; and wherein $R_2$ is hydrogen, methyl, ethyl, or fluoro; including the lower alkanoates thereof, and the pharmacologically acceptable salts thereof when $R_1$ is hydrogen.

2. A compound according to claim 1 wherein $M^{III}$ is

3. A compound according to claim 2 wherein $R_7$ and $R_8$ are either hydrogen or methyl, being the same or different, and at least one of $R_7$ and $R_8$ is methyl.

4. A compound according to claim 2 wherein $R_7$ and $R_8$ are hydrogen.

5. A compound according to claim 3 wherein $g$ is 3.

6. A compound according to claim 5 wherein $C_nH_{2n}$ has 3 carbon atoms in the chain between $-CFR_2-$ and terminal methyl.

7. A compound according to claim 6 wherein $R_2$ is hydrogen.

8. A compound according to claim 7 wherein $R_1$ is alkyl of 1 to 12 carbon atoms, inclusive.

9. A compound according to claim 7 wherein $R_1$ is hydrogen.

10. 16-Fluoro-13,14-dihydro-PGE₁, optically active compounds according to claim 9.

11. A compound according to claim 6 wherein $R_2$ is fluoro.

12. A compound according to claim 11 wherein $R_1$ is alkyl of 1 to 12 carbon atoms, inclusive.

13. 16,16-Difluoro-13,14-dihydro-PGE₁, methyl ester, an optically active compound according to claim 12 wherein $R_1$ is methyl.

14. A compound according to claim 5 wherein $C_nH_{2n}$ has 1, 2, 4, 5, or 6 carbon atoms in the chain between $-CFR_2-$ and terminal methyl.

15. A compound according to claim 4 wherein $g$ is 2, 4, or 5.

16. 2a,2b-Dihomo-16,16-difluoro-13,14-dihydro-PGE₁, a compound according to claim 15.

17. A compound according to claim 1 wherein $M^{III}$ is

* * * * *

UNITED STATES PATENT OFFICE
CERTIFICATE OF CORRECTION

Patent No. 3,969,376      Dated July 13, 1976

Inventor(s) Barney J. Magerlein

It is certified that error appears in the above-identified patent and that said Letters Patent are hereby corrected as shown below:

Column 2, line 16, for "claim 2" read -- claim 3 --.

Signed and Sealed this

Eighth Day of March 1977

[SEAL]

Attest:

RUTH C. MASON
Attesting Officer

C. MARSHALL DANN
Commissioner of Patents and Trademarks